United States Patent
Carlyle

(10) Patent No.: US 6,375,680 B1
(45) Date of Patent: *Apr. 23, 2002

(54) SUBSTRATES FOR FORMING SYNTHETIC TISSUES

(75) Inventor: Wenda C. Carlyle, Vadnais Heights, MN (US)

(73) Assignee: St. Jude Medical, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/203,052

(22) Filed: Dec. 1, 1998

(51) Int. Cl.$^7$ ............................... A61F 2/02; A61F 2/24

(52) U.S. Cl. .................... 623/11.11; 623/2.13

(58) Field of Search ............................ 623/1.41, 1.42, 623/2.13, 11.11

(56) References Cited

U.S. PATENT DOCUMENTS

| | | | |
|---|---|---|---|
| 4,648,881 A | | 3/1987 | Carpentier et al. ............ 623/11 |
| 4,786,287 A | | 11/1988 | Nashef et al. ................ 8/94.21 |
| 5,078,736 A | * | 1/1992 | Behl ............................... 623/1 |
| 5,147,514 A | | 9/1992 | Mechanic .............. 204/157.68 |
| 5,194,596 A | | 3/1993 | Tischer et al. ............... 530/399 |
| 5,258,023 A | * | 11/1993 | Reger ........................... 623/2 |
| 5,447,724 A | * | 9/1995 | Helmus et al. ............. 424/426 |
| 5,575,815 A | * | 11/1996 | Slepian et al. ................. 623/1 |
| 5,607,918 A | | 3/1997 | Eriksson et al. ............. 514/12 |
| 5,609,631 A | * | 3/1997 | Rubens et al. ................ 623/11 |
| 5,766,584 A | * | 6/1998 | Edelman et al. ............ 424/93.7 |
| 5,837,539 A | | 11/1998 | Caplan et al. .............. 435/332 |
| 5,843,172 A | * | 12/1998 | Yan ............................... 623/1 |
| 5,880,090 A | * | 3/1999 | Hammond et al. ............ 514/2 |
| 5,925,552 A | * | 7/1999 | Keogh et al. ............... 435/174 |
| 5,980,877 A | * | 11/1999 | Isner et al. ................ 424/93.7 |
| 6,024,918 A | * | 2/2000 | Hendriks et al. ............. 422/44 |
| 6,110,212 A | * | 8/2000 | Gregory .................. 623/23.72 |

FOREIGN PATENT DOCUMENTS

| | | |
|---|---|---|
| EP | 0 121 008 | 10/1984 |
| EP | 0 476 983 A1 | 3/1992 |
| EP | 0 506 477 A1 | 9/1992 |
| EP | 0 550 296 A2 | 7/1993 |
| WO | WO 95/24473 | 9/1995 |

OTHER PUBLICATIONS

"A Common Precursor for Hematopoietic and Endothelial Cells" by, Choi et al., Development 125, pp. 725–732 (1998).

"A Peptidomimetic that Specifically Inhibits Human Leukocyte Antigen DRB1*0401 Restricted T Cell Proliferation$_1$" by Woulfe et al., J. Pharm. and Exper. Therap., vol. 281, No. 2. 1997, pp. 663–669.

"A Quick, Easy and Inexpensive method for the Isolation of Human Peripheral Blood Monocytes" by, Graziani–Bowering et al., Journal of Immunological Methods 207 (1997) pp. 157–168.

"A Role for the MEK/MAPK Pathway in PMA–Induced Cell Cycle Arrest: Modulation of Megakaryocytic Differentiation of K562 Cells" by, Herrera et al., Exp. Cell Res. vol. 238, No. 2, Feb, 1, 1998, pp. 407–414 (abstract only).

"Accelerated Endothelialization by Local Delivery of Recombinant Human Vascular Endothelial Growth Factor Reduces In–Stent Intimal Formation" by, Bell et al., Biochemical and Bio Physical Research Communication 235, 311–316 (1997).

"Analysis of the Contact Sites on the CD4 Molecule with Class II MHC Molecule" by, Huang et al., Journal of Immunology, 1997, 158; pp. 216–225.

"Apparent Blood Stream Origin of Endothelial and Smooth Muscle Cells in the Neointima of Lung, Impervious Carotid––Femoral Grafts in the Dog" by, Kouchi et al., Annals of Vascular Surgery, vol. 12, No. 1, 1998, pp. 46–54.

"Activation of an Inducible c–FosER Fuse Protein Causes Loss of Epithelial Polarity and Triggers Epitheial–Fibroblastoid Cell Conversion" by, Reichmann et al., Cell, vol. 71, Dec. 24, 1992, pp. 1103–1116.

"Blood–Borne Seeding by Hematopoietic and Endothelial Precursors from the Allantois" by, Caprioli et al., Proc Natl Acad Sci USA, vol. 95, No. 4, Feb. 17, 1998, pp. 1641–1646 (abstract only).

"Cell–Cell Adhesion Molecules and the development of an Epithelial Phenotype in Cultured Human Retinal Pigment Epithelial Cells" by, McKay et al., Exp Eye Res., vol. 65, No. 5, Nov. 5, 1997, pp. 661–671 (abstract only).

"Characterization of Reticulofibroblastoid Colonies (CFU–RF) Derived From Bone Marrow and Long–Term MArrow Culture Monolayers" by, B. Lim et al., Journal of Cellular Physiology, vol. 127, 1986, pp. 45–54.

"Comparative Adhesion of Human Hemopoietic Cell Lines to Extracellular Matrix Components, Bone Marrow Stromal and Endothelial Cultures" by, Turner et al., Br J. Haematol., vol. 100, No. 1, Jan. 1998, pp. 112–122 (abstract only).

"Conditinal Switching of Vascular Endothelial Growth Factor (VEGF) Expression in Tumors: Induction of Endothelial Cell Shedding and Regression of Hemangioblastoma–like Vessels by VEGF Withdrawl" by, Benjamin et al., Proc. Natl. Acad. Sci. USA, vol. 94. pp. 8761–8766, Aug. 1997, Medical Sciences.

(List continued on next page.)

Primary Examiner—Corrine McDermott
Assistant Examiner—Hieu Phan
(74) Attorney, Agent, or Firm—Hallie A. Finucane, Esq.; Patterson, Thuente, Skaar & Christensen, P.A.; Peter S. Dardi

(57) ABSTRACT

A prosthesis is formed from a substrate with an associated attraction compound. The attraction compound binds viable precursor cells to the substrate. Thus, the substrate forms a synthetic tissue supporting viable cells once the substrate is contacted with a solution containing viable precursor cells. Preferred precursor cells differentiate into fibroblasts or into endothelial cells.

38 Claims, No Drawings

OTHER PUBLICATIONS

"Growth–Supporting Activities of Fibronectin on Hematopoietic Stem/Progenitor Cells in Vitro and in vivo: Structural Requirement for Fibronectin Activites of CS1 and CellBinding Domains" by, Yokota et al., Blood vol. 91, No. 9, May 1, 1998, pp. 3263–3272 (abstract only).

"Heterogeneity of Endothelial Cells" by, Garlanda et al, Arteriosclerosis. Thrombosis, and Vascular Biology, vol. 17, No. 7, Jul. 1997, pp. 1193–1202.

"Homing and Trafficking of Hemopoietic Progenitor Cells" by, Papayannopoulou et al., Acta Haematol 1997; 97; pp. 97–104.

"Isolation and Characterization of C–Fos–Expressing Murine Bone Marrow Stromal Cell Lines Supporting Myeloid Differentiation" by, Steff et al., Leukemia (1996) vol. 10, pp. 505–513.

"Isolation of Putative Progenitor Endothelial Cells for Angiogenesis" by, Asahara et al., Science, vol. 275, Feb. 14, 1997, pp. 964–967.

"Macrophage–Stimulating Protein, A Ligand for the RON Receptor Protein Tyrosine Kinase, Suppresses Myeloid Progenitor Cell Proliferation and Synergizes with Vascular Endothelial Cell Growth Factor and Members of the Chemokine Family" by, Broxmeyer et al., Ann. Hematol, vol. 73:1, Jul. 1996, pp. 1–9 (Abstract only).

"Migration and Proliferation of Progenitor Cells in the Connective Tissue of Rat Gingival Papilla" by, Pender et al., J Periodont Res. 1995, vol. 30, pp. 312–318.

"Mobilization and Homing of Peripheral Blood Progenitors is related to Reversible Downregulation of Alpha Beta1 Integin Expression and Function" by, Prosper et al., J. Clin. Invest., vol. 101, No. 11, Jun. 1, 1998, pp. 2456–2467 (abstract only).

"New Ligands Binding to the Human Leukocyte Antigen Classl II Molecule DRB1*0101 Based on the Activity Pattern of an Undecapeptide Library" by, Fleckenstein et al., FEBS 1996. vol.

"Novel Structural Features of the Human Histocampatibility Molecules HLA–DQ as Revealed by Modeling Based on the Published Structure of the Related Molecule HLA–DR$^1$" by, Paliakasis et al., Journal of Structural Biology 117, 145–163 (1996).

"Passivation of Metallic Stents after Arterial Gene Transfer of phVEGF$_{165}$ Inhibits Thrombus Formation and Intimal Thickening" by, VanBelle et al., J. Am. Coll. Cardiol. vol. 29, No. 6, May 1997:1371–1379.

"Possible Monocytic Origin of Chondrosarcoma: In Vitro Transdifferentiation of HLA–DR Blood Monocyte–like Cells from a Patient with Chondrosarcoma, into Neo–fibroblasts and Chondrocyte–like Cells" by, Labat et al., Biomed. & Pharmacother. 1997;51: pp. 79–93.

"Reticulo–Fibroblastoid Stromal Cell Progenitors (CFU–RF) in Murine Bone Marrow" by, Ross et al, Exp. Hematol. vol. 19, (1991) p. 1069–1074.

"Regulation of Hematopoiesis by Microvascular Endothelium" by, Rafii et al., Leuk. Lymphoma, vol. 27, No. 5–6, Nov. 1997, pp. 375–386 (abstract only).

"Relationship Between Receptor/Ligand Binding Affinity and Adhesion Strength" by, Kuo et al., Biophysical Journal, vol. 65, Nov. 1993, pp. 2191–2000.

"Stent Endothelialization: Time Course, Impact of Local Catheter Deliver, Feasibility of Recombinant Protein Administration and Response to Cytokine Expedition" by, Van Belle et al., Circulation, vol. 95. No. 2 Jan. 21, 1997, pp. 438–448.

"Stimulation of Endothelial Cell Migration by Vascular Permeability Factor/Vascular Endothelial Growth Factor through Cooperative Mechanisms Involving the $\alpha_v\beta_3$ Integrin, Osteopontin, and Thrombin" by, Senger et al., American Journal of Pathology, vol. 149, No. 1, Jul. 1996, pp. 293–305.

"Structural Motifs in Rheumatoid T–Cell Receptors" by, Kieber–Emmons et al., DNA and Cell Biology, vol. 17, No. 2, 1998, pp. 133–149.

"Synergistic Effect of Vascular Endothelial Growth Factor and Basic Fibroblast Growth Factor on Angiogenesis in Vivo" by, Asahara et al., Circulation, vol. 92, No. 9, Supplement II, Nov. 1, 1995, pp. II 365–371.

"The Expression and Differentiation Pattern of Cell Antigens and Adhesion Molecules on the Nonadherent Cell Population in Canine Long–Term Marrow Culture: A Biphasic Development of Myeloid and Lymphoid Cells" by, Krizanac–Bengez et al., Tissue Antigens, vol. 51, No. 2, Feb. 1998, pp. 141–155 (abstract only).

"Transdifferentiation of Hepatic Stellate cells (ITO Cells) to Myofibroblasts: A A Key Event in Hepatic Fibrogenesis" by, A.M. Gressner, Kidney International, vol. 49, Suppl. 54 (1996), pp. S39–S45.

"Transforming Growth Factor–Beta1 Induces Activation of Ras, Raf–1, MEK and MAPK in Rat Hepatic Stellate Cells" by, Reimann et al., FEBS Lett, vol. 403, Feb. 1997, pp. 57–60 (abstract only).

"Transmigration of CD34+ Cells across Specialized and Nonspecialized Endothelium Requires Prior Activation by Growth Factors and is Mediated by PECAM I (CD31)" by, Yong et al., Blood, vol. 91, No. 4, 1998, pp. 1196–1205 (abstract only).

"Transforming Growth Factor–Beta3 Regulates Transdifferentiation of Medial Edge Epithelium During Palatal Fusion and Associated Degradation of the Basement Membrane" by V. Kaartinen et al., Dev. Dyn., vol.209:3, Jul. 1997, pp. 255–260 (abstract only).

"Use of T Cell Receptor/HLA–DRB1*04 Molecular Modeling To Predict Site–Specific Interactions For the DR Shared Epitome Associated with Rheumatoid Arthritis" by, Penzotti et al., Arthritis & Rheumatism, vol. 40, No. 7, Jul. 1997, pp. 1316–1326.

"Using Avidin–Mediated Binding to Enhance Initial Endothelial Cell Attachment and Spreading" by, Bhat et al., J. Biomed. Mater Res., vol. 40, 1998, pp. 57–65.

"Vascular Endothelial Growth Factor and Heparin in a Biologic Glue Promotes Human Aortic Endothelial Cell Proliferation with Aortic Smooth Muscle Cell Inhibition" by, Weatherford et al., Surgery, vol. 120, No. 2, pp. 433–439 (Aug. 1996).

"Vascular Endothelial Growth Factor Inhibits Endothelial Cell Apoptosis Induced by Tumor Necrosis Factor $\alpha$: Balanced Between Growth and Death Signals" by, Spyridopoulos et al., J. Mol. Cell. Cardiol., vol. 29, 1321–1330 (1997).

"Vascular Permeability Factor/Vascular Endothelial Growth Factor Inhibits Anchorage–Disruption–Induced Apoptosis in Microvessel Endothelial Cells by Inducing Scaffold Formation" by, Watanabe et al., Experimental Cell Research 233, (1997), pp. 340–349.

"Vascular Permeability Factor/Vascular Endothelial Growth Factor (VPF/VEGF) Delays and Induces Escape from Senescence in Human Dermal Microvascular Endotheial Cells" by, Watanabe et al., Oncogene (1997) 14, 2025–2032.

* cited by examiner

SUBSTRATES FOR FORMING SYNTHETIC TISSUES

BACKGROUND OF THE INVENTION

This invention relates to the cellularization and/or recellularization of a tissue substrate or a synthetic substrate to form a synthetic tissue, which can be used in a prosthesis. More particularly, the invention relates to association of bioactive molecules with a substrate, the bioactive molecules being effective at attracting precursor cells capable of differentiating and/or transdifferentiating into fibroblasts/myofibroblasts or endothelial cells.

Prostheses, i.e., prosthetic devices, are used to repair or replace damaged or diseased organs, tissues and other structures in humans and animals. Prostheses must be generally biocompatible since they are typically implanted for extended periods of time. For example, prostheses can include artificial hearts, prosthetic heart valves, ligament repair material, vessel repair, surgical patches constructed of mammalian tissue and the like.

Prostheses can be constructed from natural materials such as tissue, synthetic materials or a combination thereof. For example, prostheses such as mechanical heart valves are manufactured from biocompatible metals, as well as other materials like graphite and polyester. Although mechanical heart valves have the advantage of proven durability through decades of use, they are associated with a high incidence of blood clotting on or around the valve. Blood clotting can lead to acute or subacute closure of the valve or the associated blood vessel. For this reason, patients with implanted mechanical heart valves remain on anticoagulants for as long as the valve remains implanted. Anticoagulants impart a 3–5% annual risk of significant bleeding and cannot be taken safely by certain individuals.

Besides mechanical heart valves, heart valve bioprostheses can be constructed from tissue components with tissue leaflets or polymer leaflets. Prosthetic tissue heart valves can be derived from porcine heart valves or manufactured from other biological material such as bovine pericardium. Biological materials in prosthetic heart valves generally have profiles and surface characteristics that provide laminar, nonturbulent blood flow. Therefore, intravascular clotting is less likely to occur than with mechanical heart valves. Unfortunately, prosthetic tissue heart valves are limited by a tendency to fail beginning about seven years following implantation. Valve degeneration is particularly rapid in young patients and during pregnancy.

Calcification, i.e., the deposition of calcium salts, especially calcium phosphate (hydroxyapatite), appears to be a major cause of degeneration in bioprostheses. Calcification of heart valve prostheses having tissue leaflets or polymer leaflets can lead to failure. Efforts to address the calcification problem have included treating glutaraldehyde-fixed valve prostheses with compounds to reduce calcium nucleation. Other approaches include use of alternative tissue fixation techniques since evidence suggests that glutaraldehyde fixation can contribute to calcification and mechanical degradation. In addition, since nonviable cells can be sites for calcium deposition, various processes have been developed to remove nonviable cells while leaving the extracellular matrix intact. Intact tissue with viable cells has natural protection against calcification.

Another major disadvantage of tissue and polymer based prostheses is their inability to regenerate. Long term durability is affected by the ability of viable cells to populate the implanted substrate and to carry out maintenance functions.

The importance of viable cells has been studied in the context of homograft transplants, i.e., transplants from one member of a species to another member of the same species. Proper homograft preservation can maximize the number of viable cells remaining in the tissue as determined by matrix protein synthesis. Preservation techniques that do not promote cell survival, such as long term storage at 4° C., are associated with reduced in vivo durability and increased reoperation rates.

The extracellular matrix is maintained by collagen secreting cells called fibroblasts. Fibroblasts are differentiated cells with a well defined morphology. They are capable of a variety of different functions depending on their association with a specific tissue. Myofibroblasts are fibroblasts that express relatively more contractile proteins such as myosin and actin. In situ, Fibroblasts reside below the endothelial monolayer that covers the surface of vascular tissue.

SUMMARY OF THE INVENTION

In a first aspect, the invention pertains to a prosthesis including a substrate with an associated attraction compound. The attraction compound binds viable fibroblast precursor cells with the substrate.

In another aspect, the invention pertains to a method of producing a prosthesis, the method comprising forming the prosthesis at least partially from a substrate with an associated attraction compound that attracts viable fibroblast precursor cells.

Moreover, the invention pertains to a kit comprising a container and instructions for the modification of a prosthesis with the attraction compound, the container holding an attraction compound, the attraction compound binding viable fibroblast precursor cells with the substrate.

In a further aspect, the invention pertains to a method for distributing a medical article for use by health care professionals, the method comprising placing a prosthesis into a package under sterile conditions and distributing the package for use by health care professionals, the prosthesis formed at least partly from a substrate with an associated attraction compound that bind viable fibroblast precursor cells.

In an additional aspect, the invention pertains to a prosthesis comprising a substrate with an associated attraction compound, the attraction compound binding viable endothelial cell precursor cells.

Furthermore, the invention pertains to a kit comprising a container and instructions for the modification of a prosthesis with the attraction compound, the container holding an attraction compound, the attraction compound binding viable endothelial cell precursor cells.

DETAILED DESCRIPTION OF THE PREFERRED EMBODIMENTS

The invention is based on the discovery that natural cellular responses can be advantageously adapted for the formation of a bioprosthesis populated with the patient's own cells. Natural tissue contains living cells that maintain the structural integrity of the tissue by resynthesizing the collagen matrix, as needed, and provide good hemodynamic performance for vascular tissues. For example, the tissue maintenance function is generally performed by fibroblasts and myofibroblasts. Fibroblasts, as used below and in the claims, include myofibroblasts. Endothelial cells line vascular tissue and improve hemodynamic performance.

In general, relevant medical devices are bioprostheses that are formed to mimic a corresponding structure within the body. The bioprostheses can be used to replace the corresponding native structure. The medical devices can be prosthetic devices suitable for long term implantation within a recipient patient. The medical devices include a substrate that is formed from a natural tissue and/or from a synthetic material. The substrate includes a bioactive molecule that attracts the precursor cells to the substrate. These bioactive molecules capable of attracting fibroblast and/or endothelial cell precursors are referred to herein as attraction compounds. Attraction compounds interact with precursor cells such that the cells are bound to the substrate. Using the patient's own cells to populate the substrate avoids the possibility of rejection of the prosthesis by the patient's immune system. Generally, the patient is an animal, preferably a mammal, such as a human.

Precursor cells include both progenitor cells that can mature into fibroblasts or endothelial cells, and cells that can differentiate or transdifferentiate into fibroblasts or endothelial cells. Precursor cells circulate in a patient's blood stream. These precursor cells are thus available to colonize suitable blood contacting substrates. Suitable precursor cells can be selected from the blood stream and associated with a substrate that serves as the foundation for a viable prosthetic tissue. To initiate the colonization of the precursor cells, an attraction compound is associated with the substrate. Circulating precursor cells are removed from circulation by the attraction compound and become associated with the substrate.

Monocytes and macrophages with a HLA-DR marker on their surfaces are capable of transdifferentiating into fibroblasts. This is described in M. L. Labat et al., "Possible monocytic origin of chondrosarcoma: in vitro transdifferentiation of HLA-DR blood monocyte-like cells from a patient with chondrosarcoma, into neo-fibroblasts and chondrocyte-like cells," Biomed. & Pharmacother 51: 79–93 (1997), incorporated herein by reference. The HLA-DR marker is a protein complex. The properties of the HLA-DR marker are described in J. Townsdale et al., "Complexity in the major histocompatibility complex," Eur. J. Immunogenet. 19:43–55 (1992) and H. K. Ziegler et al., "Identification of a macrophage antigen processing event required for I-region restricted antigen presentation to T lymphocytes," J. Immunol. 127:1869–1875 (1981), both of which are incorporated herein by reference.

In some preferred embodiments of the invention, the HLA-DR marker is used to select for preferred precursor monocytes/macrophages. Monocytes/macrophages with a HLA-DR marker can transdifferentiate spontaneously into fibroblasts, under some circumstances. Antibodies or ligands directed against the HLA-DR marker can serve to bind these monocytes to the substrate. In addition, response modifiers can be associated with the substrate. For example, effector molecules can be associated with the substrate to inhibit a macrophage mediated inflammatory response that could lead to undesirable complications. With respect to other response modifiers, specific cytokines can be associated with the substrate to encourage the differentiation of macrophages into fibroblasts. Thus, both attraction compounds and effector compounds may be associated with the substrate.

Precursors for endothelial cells, called angioblasts, are also found in the blood stream. In some preferred embodiments, ligands for the endothelial cell surface marker, endoglin, are used as attraction compounds to select for preferred endothelial cell precursors.

Medical devices are formed such that a substrate within the device is populated with viable fibroblasts and/or endothelial cells when exposed to suitable precursor cells. In this way, increased longevity of the device can result from tissue maintenance performed by the fibroblasts within the prosthetic tissue. The association of endothelial cells with the substrate can maintain the hemodynamic performance of the device over time while decreasing available surface areas that are prone to calcification. Thus, the attraction of viable cells to a substrate within the prosthesis should improve the long term viability of the medical device.

The attraction compounds can be associated with the substrate before or after the substrate is formed into the prosthesis. The prosthesis can be implanted into the patient such that precursor cells circulating in the patient's blood stream make contact with the prosthesis and bind to the attraction compounds.

Alternatively, the substrate can be contacted with a solution in vitro containing precursor cells obtained from a patient to populate the substrate with precursor cells. The precursor cells generally can be harvested from the patient's blood or bone marrow using a variety of techniques.

Addition of a bioactive molecule capable of attracting fibroblast precursors to colonize the interior of the valve matrix can provide for a prosthesis that is capable of regenerating extracellular matrix proteins as needed to maintain tissue durability. These fibroblasts also can provide the tissue with a means to remodel or grow in response to demands by the host. Similarly, incorporation of a bioactive molecule capable of attracting precursor cells that can develop into endothelial cells on the surface of a mechanical heart valve or a portion thereof could reduce the risk of thrombosis and the long-term need for anticoagulation therapy. Also, modification of the tissue with agents that promote endothelialization can provide the tissue with a barrier against calcification. Since both endothelial cells and fibroblasts can stimulate the clean-up of non-viable cells and prevent calcium nucleation, modifications that promote colonization of the tissue by these cells can reduce calcification and improve prosthesis durability.

Prostheses

Prostheses can include a tissue substrate, a synthetic substrate or a combination thereof, such that the substrate is suitable as a location for cellular attachment. Generally, these prostheses are designed for implantation into or onto a patient for extended periods of time. Prostheses include, for example, artificial hearts, artificial heart valves, annuloplasty rings, pericardial patches, vascular and structural stents, vascular grafts, pledgets, suture, leads, permanently in-dwelling percutaneous devices, vascular or cardiovascular shunts, dermal grafts for wound healing, and surgical patches. The approaches described herein are particularly appropriate with uncrosslinked autografts or homografts, such as heart valve prostheses. Biomedical devices that are designed to dwell for extended periods of time within a patient are also suitable to include attraction compounds. These devices include, for example, Hickman catheters.

Substrates

Appropriate substrates can be formed from natural materials, synthetic materials and combinations thereof. Natural, i.e. biological, material for use in the invention includes relatively intact tissue as well as decellularized tissue. These tissues may be obtained from, for example, natural heart valves, portions of natural heart valves such as roots, walls and leaflets, pericardial tissues such as pericardial patches, connective tissues, bypass grafts, tendons, ligaments, skin patches, blood vessels, cartilage, dura mater, skin, bone, fascia, submucosa, umbilical tissues, and the like.

Natural tissues are derived from a particular animal species, typically mammalian, such as human, bovine, porcine, canine, seal or kangaroo. These tissues may include the whole organ, including homografts and autografts. These natural tissues generally include collagen-containing material. Natural tissue is typically, but not necessarily, soft tissue. Tissue materials are particularly useful for the formation of tissue heart valve prostheses. The tissue can be decellularized. Decellularization approaches are described, for example, in published PCT Applications WO96/03093 and WO96/32905, both incorporated herein by reference.

Tissues can be fixed by crosslinking. Fixation provides mechanical stabilization, for example, by preventing enzymatic degradation of the tissue. Glutaraldehyde or formaldehyde is typically used for fixation, but other fixatives can be used, such as epoxides and other difunctional aldehydes. Tissues can be used in either crosslinked or uncrosslinked form, depending on the type of tissue, the use and other factors.

Generally, if xenograft tissue is used, the tissue is crosslinked and/or decellularized. Alternatively, xenograft tissue from transgenic animals can be used as a substrate. These transgenic donor animals may be genetically altered so as not to express antigens and complement activating proteins that might stimulate an immune response or rejection by the recipient. An example of this type of tissue is porcine tissue from animals lacking the gene to express the Gal$\alpha$1-3Gal antigen responsible for much of the hyperacute rejection response.

Relevant synthetic materials include, for example, polymers and ceramics. Appropriate ceramics include, without limitation, hydroxyapatite, alumina and pyrolytic carbon. Ceramics can be coated with a polymer, protein or other compound prior to use as a substrate, if desired. Polymeric materials can be fabricated from synthetic polymers as well as purified biological polymers. Appropriate synthetic materials include hydrogels and other synthetic materials that cannot withstand severe dehydration.

Appropriate synthetic polymers include without limitation polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. These synthetic polymeric materials can be woven or knitted into a mesh to form a matrix or substrate. Alternatively, the synthetic polymer materials can be molded or cast into appropriate forms.

Biological polymers can be naturally occurring or produced in vitro by fermentation and the like or by recombinant genetic engineering. Recombinant DNA technology can be used to engineer virtually any polypeptide sequence and then amplify and express the protein in either bacterial or mammalian cells. Purified biological polymers can be appropriately formed into a substrate by techniques such as weaving, knitting, casting, molding, extrusion, cellular alignment and magnetic alignment. For a description of magnetic alignments see, for example, R. T. Tranquillo et al., Biomaterials 17:349–357 (1996). Suitable biological polymers include, without limitation, collagen, elastin, silk, keratin, gelatin, polyamino acids, cat gut sutures, polysaccharides (e.g., cellulose and starch) and copolymers thereof.

The substrate can form the entire medical device or it can form portions of the medical device. Similarly, different substrates can be combined to form the medical device. For example, a tissue heart valve can be combined with a fabric sewing cuff to form a heart valve prosthesis, where the tissue and/or the fabric can be a substrate from the perspective of introducing attraction compounds. In other words, the tissue and/or the sewing cuff can be associated with one or more attraction compounds. The attraction compounds can be associated with the substrate before or after the various components are combined into the medical device. The selected approaches for association of the attraction molecules with the substrate or substrates may influence the order of construction of the medical device.

Attraction Compounds

Attraction compounds, i.e. attraction molecules, are associated with the substrate to bind desirable precursor cells to the substrate. Thus, the attraction compound can attract fibroblast precursors, such as monocytes/macrophages or fibroblast progenator cells, or endothelial cell precursors, such as angioblasts. If desired, a plurality of attraction compounds can be used, possibly directed to different cell types.

When monocytes move from the blood into a tissue, they are termed macrophages. Macrophages can take part in immune responses to infection or invasion by foreign bodies. Under special circumstances, macrophages can transdifferentiate into other cell types, including fibroblasts. Thus, suitable precursor cells for the subsequent colonization of fibroblasts include monocytes and macrophages.

While the attraction compounds can be selected to attract any precursor cells, in some preferred embodiments, the attraction compounds are selected to attract specific monocytes/macrophages that are more likely to transdifferentiate into fibroblasts. In particular, monocytes/macrophages having a HLA-DR marker can transdifferentiate into fibroblasts and secrete collagen.

HLA-DR attractants include all molecules with an affinity for the HLA-DR marker. In particular, suitable HLA-DR attractants include antibodies raised against HLA-DR antigens. Suitable antibodies include monoclonal antibodies and polyclonal antibodies. Preferred HLA-DR antibodies include antibody fragments with the Fab portion of the antibody and humanized antibodies. Generally, antibodies are generated against human HLA-DR antigens in non-human animals including, for example, chickens, mice and rabbits. These antibodies can be humanized by integrating the antigen binding surface into the framework of a human antibody variable region. Humanized antibodies are less likely to create an immune response in the recipient patient. Antibodies can be humanized according to procedures described, for example, in C. Rader, et al., "A phage display approach for rapid antibody humanization: designed combinatorial V gene libraries," Proc. Natl. Acad. Sci USA 95(15): 8910–8915 (1998), incorporated herein by reference. Using recombinant DNA technology, antibodies also can be made by expression of human genes in mammalian cell systems. Human HLA-DR antibodies are available from Ortho Diagnostics, Raritan, N.J.

Alternatively, other attraction compounds/ligands for the HLA-DR marker can be used. In particular, natural ligands or relevant portions of natural ligands can be used as attraction compounds. For example, the following ligands for the HLA-DR marker are known: CD4, L plastin p581–595 peptide, CLIP (class II—associated chain peptides), HSP-70 (heat shock protein) and TCR (T-cell receptor). Also, given the known structure of the HLA-DR marker, suitable ligands can be synthesized based on established chemical principles. Suitable ligands can be designed based on procedures described in the following references: B. Fleckenstein et al., Eur. J. Biochem. 240(1): 71-7 (1996), S. L. Woulfe et al., J. Pharmacol. Exp. Therapeutics 281(2): 663–9 (May 1997), K. Paliakasis et al., J. Structural Biolog. 117(2): 145–63 (September 1996), B. Huang, J. Immunology 158(1): 216–25 (January 1997), J. E. Penzotti et al., Arthritis Rheum. 40(7): 1316–26 (July 1997), and E. T. Keiben et al., DNA Cell Biol. 17(2): 133–49 (Febuary 1998), all of which are incorporated herein by reference. The binding affinities between the HLA-DR marker and a putative ligand can be evaluated using established techniques.

Similarly, combinatorial chemistry approaches can be used to screen a set of putative ligands to find a ligand with a suitable binding affinity. In combinatorial chemistry approaches, a set of putative ligands are evaluated for effectiveness such that relevant structures within a ligand can be identified. The putative ligands can be selected based on chemical principles or by analogy with known binding molecules. Further refinements can be made based on information gained from a particular set of putative ligands.

As an alternative to attracting monocytes or macrophages capable of transdifferentiating into fibroblasts, different attraction compounds can be used to attract fibroblast progenator cells. Fibroblast progenator cells have been termed fibroblastoid cells or fibroblast colony-forming cells (CFU-F). Such cells have been isolated from bone marrow, as described in H. Castro-Malaspina et al., "Characterization of human bone marrow fibroblast colony forming cells (CFU-F) and their progeny," Blood 56:289–301 (1980), incorporated herein by reference. The progeny of CFU-F synthesize collagen types I and III. Antibodies raised against surface antigens present on the CFU-F would serve as suitable attraction compounds to bind these fibroblast precursor cells. An example of one of these antibodies, termed HOP-26, and a method for developing the antibodies are described in a reference by C. J. Joyner et al., "Identification and enrichment of human osteoprogenitor cells by using differentiation stage-specific monoclonal antibodies," Bone 21(1) :1–6 (1997), incorporated herein by reference.

In other preferred embodiments, endothelial cell precursors are selected on the basis of cell surface antigens such as CD34, endoglin, Flk-1, eselectin or CD31. Antibodies or fragments thereof directed against cell surface antigens can be used as attraction compounds. Similarly, natural ligands or portions thereof for cell surface receptors on endothelial cell precursors can be used to form attraction compounds. Attraction compounds can be ligands for angioblast cell surface receptors.

In summary, attraction compounds of a variety of different types can be used to associate precursor cells such as monocytes/macrophages, fibroblast progenitor cells and/or angioblasts with a substrate. Preferred attraction compounds for fibroblast precursor cells have an affinity for the HLA-DR marker or cell surface antigens of fibroblast progenitor cells. Suitable attraction compounds for endothelial cell precursors similarly have an affinity for corresponding cell surface antigens. Preferred attraction compounds include, for example, antibodies or portions thereof and receptors (ligands) or portions thereof, either natural or synthetic.

The usefulness of an attraction compound/ligand for attracting precursor cells can be determined empirically by assessing specificity for desired precursor cells, affinity for cell surface receptors, the number of potential binding sites on the cell and the ability of the compound to bind cells tightly enough so that they can withstand shear stress and remain bound. A ligand's ability to select and attract a desired precursor cell from whole blood can be assessed by, for example, the method described in Asahara et al., "Isolation of Putative Progenitor Endothelial Cells for Angiogenesis," Science 275:964–967 (1997), incorporated herein by reference. In the method of Asahara et al., magnetic beads are coated with the ligand and incubated with either whole blood or the leukocyte fraction. The magnetic beads are used to draw cells bound to the beads out of solution. Once detached from the beads, the isolated cells are fluorescently labeled with an antibody directed against a cell surface receptor specific for the precursor cell of interest. Fluorescence-activated cell sorting can be performed to assess the percentage of cells bearing the appropriate marker. Other methods for determining ligand specificity for a particular precursor cell type also may be used.

Ligand binding affinity generally reflects the cumulative effect of many relatively weak non-covalent interactions, including hydrophobic interactions, hydrogen bonds, van der Waals forces and ionic interactions. The affinity constant can be measured as the concentration of free ligand required to fill half of the binding sites associated with a particular receptor. Thus, the lower the affinity constant, the greater the attraction or binding strength. The affinity constant of a ligand used for binding a receptor on the precursor cell surface preferably is less than about $10^{-8}$ moles/liter, and more preferably less than about $10^{-10}$ moles/liter. Stronger (i.e., smaller) affinity constants should provide stability for long-term attachment.

In general, adhesion strength varies with the logarithm of the binding affinity constant, as described by Kuo et al., Biophysical J. 65:2191–2200 (1993), incorporated herein by reference. As noted above, antibodies directed against specific precursor cell surface receptors can be used as ligands. Antibodies may be particularly effective as ligands because they can have affinity constants less than $10^{-10}$ moles/liter, and in particular, in the range from $10^{-10}$ to $10^{-11}$ moles/liter. In addition, antibodies can have the ability to form multiple bonds, increasing avidity for the receptor by a thousand-fold or greater. The affinity for a receptor can be determined by standard approaches, such as competitive binding assays.

Binding effectiveness reflects both affinity and number of binding sites. Many growth factors and cytokines have very strong affinities for their respective receptors but may have limited usefulness due to the scarcity of their receptors on the surface of precursor cells. Growth factors and cytokines may also stimulate unwanted cellular responses in addition to the desired attachment response.

An additional test for determining the usefulness of a ligand is the ligand's ability to prevent cell detachment under conditions of physiologic flow or shear stress. An assay for assessing this parameter is described in detail in Bhat et al., J. Biomed. Mater. Res. 40: 57–65 (1998), incorporated herein by reference. A modification of the Bhat et al. assay to assess the ability of a ligand to attract a particular precursor cell involves attaching the ligand to the surface of a slide, seeding precursor cells on the slide surface with attached ligands, and placing the slide in a flow chamber. The flow chamber can be mounted on the stage of an inverted microscope equipped with a video camera for monitoring and quantifying cell association. Flow of a liquid medium is directed over the slide. Then, the percentage of cells detached during a specified period with a specified rate of flow can be determined. Alternatively, the liquid medium flowing over the slide can have suspended precursor cells in it. The ability of the cells to attach to the ligands on the glass slides can be quantified. By the approaches described above or other suitable methods, suitable ligands can be assessed for their ability to bind and attach precursor cells to the surface of a synthetic or tissue-based substrate.

Response Modifiers

Once the precursor cells are associated with the substrate, it is desirable for the cells to differentiate or transdifferentiate into the appropriate cell types. In preferred embodiments, the substrate also is associated with compounds (promotion compounds) that promote this differentiation. In embodiments where HLA-DR presenting macrophages are attracted to the substrate, it is preferable to include additional associated compounds (inhibition compounds) that inhibit a macrophage-mediated inflammatory response. Promotion compounds and inhibition compounds are collectively referred to as response modifiers.

In some preferred embodiments, vascular endothelial growth factor (VEGF) is associated with the substrate in addition to an attraction compound binding endothelial progenitor cells. The attraction compound attaches the endothelial cells to the surface of the substrate, and VEGF promotes the differentiation of the progenitor cells to mature endothelial cells. VEGF can also stimulate the growth as well as the differentiation of endothelial cells. Thus, VEGF is an example of a promotion compound. VEGF can also bind endothelial cell precursors. Therefore, VEGF can act as an attraction compound, although endothelial cell precursors have relatively few receptors that bind to VEGF.

Other response modifiers consist of those agents capable of stimulating the growth or maturation of fibroblasts precursor cells. An example of this type of modifier includes substance P, which can be used alone or in combination with other response modifiers such as platelet-derived growth factor-BB (PDGF-BB) and interleukin-1alpha (IL-1α) to stimulate growth of fibroblasts from bone marrow derived progenitor cells, as described in P. Rameshwar et al., "Receptor induction regulates the synergistic effects of substance P with IL-1 and platelet-derived growth factor. on the proliferation of bone marrow fibroblasts," J. Immunol. 158 (7): 3417–3424 (1997).

Macrophages are known to transdifferentiate into a variety of cell types including fibroblasts, osteoblasts, myofibroblasts, and chondrocytes. While these transdifferentiation events often occur under pathological conditions, the transition of macrophages to fibroblasts can occur spontaneously. If some of the associated macrophages transdifferentiate into fibroblasts, others may remain as macrophages. It is advantageous to prevent the remaining macrophages from generating an inflammatory response. In a preferred embodiment, additional proteins are associated with the substrate that modulate macrophage phenotype to inhibit the inflammatory and cytocidal response. Thus, these inhibitory proteins are inhibition compounds.

One inhibitory protein is osteopontin. Osteopontin can favorably influence a number of macrophage functions. First, it can recruit monocytes from circulation. Osteopontin can prevent the monocytes from becoming activated macrophages and giant cells. Furthermore, osteopontin can promote retention, survival and proliferation of differentiated macrophages within the substrate. Also, osteopontin can inhibit the release of cytokines from macrophages. In summary, an inhibitory compound, such as osteopontin, can be associated with the substrate along with the attraction compound to inhibit an undesirable response, such as an inflammatory response.

Association of Compositions with the Substrate

The substrate generally has one or more attraction compounds associated with it. In preferred embodiments, the substrate further has one or more inhibition compounds to inhibit an inflammatory response and/or promotion compounds to promote differentiation into desired cell types.

The association of an attraction compound (attractant) or a response modifier with a substrate each may involve direct attachment, application of a coating including an adhesive or binder, or chemical binding involving a binding agent in addition to the attraction compound/response modifier.

Direct attachment entails combining the substrate with a solution of the attractant/response modifier, i.e., attraction compound(s) and/or response modifier(s), without the use of an additional chemical binder. Due to direct contact, the attractant/response modifier can bind with the substrate. For direct binding of the attractant/response modifier to the substrate, the substrate or a portion thereof is combined with a solution of the attractant/response modifier at a concentration generally from about 1 ng/ml to about 100 μg/ml and preferably from about 25 ng/ml to about 10 μg/ml. Individual attractants and response modifiers in the solution can be incorporated at different concentrations.

For natural tissue based or synthetic substrates, the solution containing the attractant/response modifier preferably is buffered at a near physiological pH ranging from about 6.0 to about 8.5, and more preferably ranging from about 6.9 to about 7.5. Suitable buffers can be based on, for example, the following compounds: phosphate, borate, bicarbonate, carbonate, cacodylate, citrate, and other organic buffers such as tris (hydroxymethyl) aminomethane (TRIS), N-(2-hydroxyethyl) piperazine-N'-(2-ethanesulfonic acid) (HEPES), and morpholine propanesulphonic acid (MOPS).

Alternatively, the attractant/response modifier can be associated with the substrate through the use of a binder or adhesive. The attractant/response modifier associates with the substrate due to incorporation into the structure of the adhesive when the adhesive cures. The attractant/response modifier and the adhesive form a coating on the substrate. Preferred adhesives include, for example, biologic glues such as fibrin glue, and the like. Fibrin glue can be formed from the polymerization of fibrinogen and thrombin. Suitable fibrin glues are available from, for example, Immuno AG, Austria and Zymogenetics, Seattle, Wash.

To apply the attractant/response modifier with a fibrin glue to tissue or synthetic substrates, a small amount of thrombin can be absorbed into the substrate. The attractant/response modifier can be mixed with a solution containing fibrinogen to yield a fibrinogen-attractant/response modifier solution with a concentration of the attractant/response modifier preferably ranging from about 1 ng/ml-100 μg/ml. Then, the fibrinogen-attractant/response modifier mixture can be brushed over the surface of the substrate with absorbed thrombin, or the substrate with absorbed thrombin can be dipped into the fibrinogen-attractant/response modifier solution. The coating can be applied to all or just a portion of the substrate. With synthetic substrates, the attractant/response modifier also can be incorporated into the substrate material when the substrate is formed. When incorporated into the substrate material, the attractant/response modifier preferably is bound tightly with the substrate and can be located in interstitial spaces within the substrate material.

In other embodiments, the association of an attractant/response modifier with the substrate involves chemical binding initiated by a selected chemical reagent, a chemical binding agent. In contrast with the use of an adhesive, chemical binding involves specific molecular interactions with substrate compositions, rather than a collective adhesion. Chemical binding can involve covalent bonding, a plurality of noncovalent chemical interactions, or a combination of both covalent and noncovalent interactions. Noncovalent chemical interactions include hydrogen bonding, van der Waals interactions and molecular rearrangements, which characterize specific binding interactions, such as antibody-antigen interactions, protein-receptor binding and enzyme-substrate associations. In other words, reactants or binding agents are used to form a chemical association between the attractant/response modifier and the substrate, possibly involving a linker molecule. For tissue or synthetic substrates, the chemical binding of the attractant/response modifier preferably takes place at or near physiological pH, preferably ranging from a pH of about 6 to about 8.5 and more preferably from about 6.9 to about 7.5.

The chemical binding of the attractant/response modifier with the substrate can involve covalent bonding to the surface of the substrate with reactive agents such as glutaraldehyde and other suitable crosslinking agents. This is an especially suitable procedure for binding polypeptide attractant/response modifiers (such as antibodies) with substrates formed from tissue or other polymers with suitable functional groups. A typical procedure for the crosslinking of the attractant/response modifier to the surface of a tissue makes use of glutaraldehyde, which crosslinks proteins by way of two aldehyde groups. Since glutaraldehyde is typically used for fixation of tissue, the crosslinking to bind the attractant/response modifier to the tissue can be performed simultaneously with fixation of the tissue. Alternatively, crosslinking to covalently bond the attractant/response modifier with a tissue or synthetic substrate can be performed as a separate step before or after the completion of a fixation process, assuming a fixation step is performed. Other chemical reagents for covalent bonding of attractant/response modifiers to a substrate include, for example, epoxies.

Alternatively, chemical binding of the attractant/response modifier to the substrate can involve specific binding interactions. If selected accordingly, the specific binding interactions can be used to target specific locations within the substrate. The targeting of specific locations in the substrate can be useful, for example, if specific locations are resistant to colonization by the desired cell type or if colonization by the selected cells is particularly beneficial at specific locations. An example of a possible target location includes heart valve leaflets.

One method of targeting a particular location involves the use of linkers that target specific cellular or extracellular binding sites within a natural tissue/substrate. In certain embodiments, the linker is covalently bound to the attractant/response modifier molecule, and the linker associates with the tissue by a plurality of non-covalent interactions such as antibody-antigen interactions. Alternatively, the linker can be covalently bound to the substrate and the attractant/response modifier molecule can be associated with the linker by a plurality of non-covalent interactions. A variety of commercially available antibodies and other specific binding reagents may be used as linkers. Alternatively, antibodies and other specific binding reagents can be prepared by conventional techniques.

An attractant/response modifier molecule having an attached antibody or any other comparable targeting molecule or an engineered chimera of the attractant/response modifier molecule and the targeting molecule is considered an attractant/response modifier for the purposes of the present application. The chemical binding of compounds to antibodies as well as the development of chimeras is well established, especially where the compound is a protein. Empirical adjustments can be made to ensure that the activity of the attractant/response modifier molecule is not significantly impaired.

In an alternative embodiment, photochemical coupling can be used for covalent coupling. Photochemical coupling is based on the use of high energy light, e.g., ultraviolet light, to form reactive intermediates of certain functional groups. These reactive intermediates can form carbon-carbon bonds between two compositions. Aryl ketone functional groups are particularly useful in this respect.

Photochemical coupling can be used for attachment of attractant/response modifiers to tissue. See, for example, Dunkirk et al., J. Biomaterials Applications 6:131–156 (1991), incorporated herein by reference. The tissue may or may not be separately crosslinked since the photochemical coupling generally also crosslinks the tissue, i.e., photofixation. Alternatively, photochemical coupling can be used to attach a linker to the tissue either before, after, or during binding of the linker to an attractant/response modifier molecule.

Regardless of the nature of the interaction between the substrate and the attractant/response modifier, the bound attractant/response modifier molecules generally are in equilibrium with unbound molecules. As a result, the attractant/response modifier molecules may eventually be lost to the surrounding solution if the solution is replenished. For some applications it may be sufficient for the attractant/response modifier molecules to be bound for a relatively short period of time, such as hours or days if sufficient viable fibroblasts and/or endothelial cells proliferate on the tissue during the relevant time. In other circumstances, it may be desirable to have longer term binding of the attractant/response modifier to the tissue, such as months or years. A suitable approach for associating the attractant/response modifier molecule with the substrate can be selected based on binding constants, the conditions to which the substrate will be subjected and the desired length of time for binding.

If suitable, the attraction compound and any response modifier can be bound simultaneously to the substrate. If the attraction compound and the response modifier are significantly different chemically, it may not be practical to bind them simultaneously. Based on the particular binding approach selected for the individual compounds, the order of binding may be significant. The binding approaches may need to be altered in order to be compatible. Binding approaches can be evaluated empirically to determine the efficacy of the binding and the appropriate order for processing.

Combination with Antimicrobials

The implantation of a prosthesis can be associated with a risk of infection. Such infections can be life threatening and may require replacement of the prosthesis. Thus, it is useful to treat the medical device to reduce the risk of such an infection.

The association of endothelial cells with a prosthesis should reduce the risk of long term infection by the elimination of surfaces suitable for the attachment of microorganisms. Nonetheless, not all portions of the prosthesis may have associated viable cells, and there still may be short term risks of infection that can be extremely serious.

As a minimal precaution to reduce the risk of infection, the prosthesis is produced free of microorganisms. This can be done using antiseptic production approaches and/or through the use of sterilization techniques. Additionally, the prosthesis can be rinsed in an antiseptic solution immediately prior to use. These approaches, though, generally provide only very short term protection. Other antimicrobial approaches can be used although the approach should be consistent with the eventual population of the matrix with selected cells.

A particularly suitable approach to associate an antimicrobial agent with the substrate without disrupting the association of selected cells involves the use of exogenous storage structures. Exogenous storage structures are not inherent to the substrate to which they are attached. In other words, the exogenous storage structures are in addition or an alternative to any naturally occurring structures that are inherently part of the substrate structure. Exogenous storage structures are attached to the substrate at a molecular level without necessarily forming a coating that may disrupt either the attachment of a attraction compound or the precursor cells themselves. The exogenous storage structures can store significant quantities of antimicrobial agents. In a particularly preferred embodiment, the exogenous storage structure is a metal binding protein, such as ferritin, and the antimicrobial agent is silver ions or other antimicrobial metal ions. The exogenous storage structure can be bound to the substrate, for example, by crosslinking or using antibodies. A more complete description of the use of exogenous storage structures for the delivery of antimicrobial agents can be found in copending and commonly assigned U.S. patent application Ser. No. 08/787,139 to Tweden et al., entitled "Medical Article with Adhered Antimicrobial Metal Ions and Related Methods," incorporated herein by reference.

Alternatively, a coating of antimicrobial agents can be placed on the substrate. In addition, if a portion of the prosthesis is not associated with attraction compounds, that portion can be coated with an antimicrobial agent to reduce the risk of infection. The association of antimicrobial elemental metal (such as silver metal) and/or antimicrobial metal compounds (such as silver chloride) with a biocompatible material is described in copending and commonly assigned U.S. patent application Ser. No. 08/974,992 to Ogle, entitled "Medical Article with Adhered Antimicrobial Metal," incorporated herein by reference, and U.S. patent application Ser. No. 09/143,989 to Ogle et al., entitled "Medical Article with Adhered Antimicrobial Metal," incorporated herein by reference.

Combination with Anticalcification Compounds

The association of endothelial cells and possibly fibroblasts with a substrate would be expected to reduce the calcification of the substrate subsequent to implantation. Nevertheless, it may be desirable to associate anticalcification agents with the substrate to further reduce the calcification of the substrate or to reduce calcification of portions of the substrate lacking viable cells.

A particularly suitable approach to associate an anticalcification agent with the substrate without disrupting the association of selected cells with the substrate involves the use of exogenous storage structures comparable to those described above with respect to antimicrobial agents. Exogenous storage structures are attached to the substrate at a molecular level without necessarily forming a coating that may disrupt either the attachment of an attraction compound or the precursor cells themselves. The exogenous storage structures can store significant quantities of anticalcification agents. In a preferred embodiment, the exogenous storage structure is a metal binding protein, such as ferritin, and the anticalcific agent is trivalent aluminum ions or other anticalcific metal ions. The exogenous storage structure can be bound to the substrate, for example, by crosslinking or using antibodies.

A more complete description of the use of exogenous storage structures for the delivery of anticalcification agents can be found in copending and commonly assigned U.S. patent application Ser. No. 08/931,930 to Schroeder et al., entitled "Calcification Resistant Biomaterials," incorporated herein by reference, and copending and commonly assigned U.S. patent application Ser. No. 08/690,661 to Schroeder et al., entitled "Calcification Resistant Biomaterials," incorporated herein by reference.

Packaging, Distribution and use

Following binding of the attractant/response modifier to the substrate, the substrate, possibly formed into a prosthesis, can be stored. The substrate preferably would not have ingrowth of viable cells if the substrate is intended for longer term storage. Preferred storage techniques minimize the risk of microbial contamination. For example, the biocompatible material can be stored in a sealed container with sterile buffer and/or saline solution.

In a sealed container the biocompatible material is not subjected to a continuous supply of fluids. Nevertheless, consideration should be given to possible loss during storage of attractant/response modifier from the substrate or loss during storage of activity of the attractant/response modifier. If excessive loss is a possibility, the storage time can be limited appropriately to keep the loss to an acceptable level. For distribution, the prosthesis generally is placed in sealed and sterile containers. The containers can be dated such that the date reflects the maximum advisable storage time accounting for possible loss of compound or degradation of activity. The containers generally are packaged with instructions for the use of the medical devices along with desired and/or required labels. The containers are distributed to health care professionals for surgical implantation of the prostheses. The implantation is performed by a qualified health care professional. The surgical implantation generally involves the replacement of damaged tissue with the prosthesis.

As an alternative to the above storage and distribution approaches, the modification of the substrate by addition of an attractant/response modifier can be performed at a hospital or site remote from the manufacturing site, if desired. This is a particularly suitable approach if the storage time for the substrate modified with the attractant/response modifier is short. Then, the prosthesis prepared for modification is distributed with a solution of the attractant/response modifier. Alternatively, a solution of the attractant/response modifier is distributed separately from the prosthesis along with instructions for performing substrate modification, packaged together as a kit. For embodiments based on chemical binding or adhesive attachment, a kit can be distributed comprising a container of the attractant/response modifier and a separate container of a chemical binding agent or an adhesive together in a package, optionally along with instructions for modification of a substrate. Then, a selected prosthesis can be modified using the compositions from the kit prior to implantation. Once the prosthesis is modified with the attractant/response modifier, it can be implanted, stored for a reasonable period of time or introduced into a cell culture system to affiliate autologous cells with the attractant/response modifier—modified prosthesis.

In vitro affiliation of cells with a modified substrate/prosthesis preferably is performed at hospitals where the patient's cells can be removed for use in a cell culture system. The cells can be harvested from the patient's blood or bone marrow. The harvested cells can be contacted with the substrate in a cell culture system to associate the cells with the substrate. Thus, a synthetic tissue is formed based on cells from the patient prior to implantation.

Incorporation of an attraction compound into a prosthesis to promote endothelialization of a substrate should improve biocompatibility of the substrate following implantation. In particular, viable cells can serve as a barrier to infection, inflammation, and calcification. Incorporation of an attraction compound into a prosthesis to promote fibroblast colonization should allow for regeneration of matrix proteins as needed to maintain the integrity of the prosthesis. Thus, the durability and the longevity of a prosthesis can be significantly improved. Ultimately, cellularization of a suitable substrate can provide for a prosthesis that more closely resembles a native, biologically competent tissue.

The embodiments described above are intended to be exemplary and not limiting. Further embodiments are within the claims below. Although the present invention has been described with reference to preferred embodiments, workers skilled in the art will recognize that changes may be made in form and detail without departing from the spirit and scope of the invention.

What is claimed is:

1. A prosthesis comprising a substrate with an associated attraction compound, the attraction compound binding viable fibroblast precursor cells with the substrate, wherein the attraction compound is not a growth factor.

2. The prosthesis of claim 1 wherein the prosthesis is a heart valve prosthesis.

3. The prosthesis of claim 1 wherein the prosthesis is a vascular prosthesis.

4. The prosthesis of claim 1 wherein the substrate comprises a tissue.

5. The prosthesis of claim 1 wherein the substrate comprises uncrosslinked tissue.

6. The prosthesis of claim 1 wherein the substrate comprises a bioresorbable polymer.

7. The prosthesis of claim 1 wherein the substrate comprises a fabric.

8. The prosthesis of claim 7 wherein the fabric comprises synthetic polymers.

9. The prosthesis of claim 1 wherein the attraction compound comprises antibodies.

10. The prosthesis of claim 9 wherein the antibodies exhibit some specificity for precursor cells expressing HLA-DR specificity.

11. A method for distributing a medical article for use by health care professionals, the method comprising placing a prosthesis of claim 1 into a package under sterile conditions and distributing the package for use by health care professionals.

12. The prosthesis of claim 1 wherein a growth factor, distinct from the attraction compound, is associated with the substrate.

13. A method of producing a prosthesis, the method comprising forming the prosthesis at least partially from a substrate with an associated attraction compound that attracts viable fibroblast precursor cells, wherein the attraction compound is not a growth factor.

14. The method of claim 13 wherein the prosthesis is a heart valve prosthesis and wherein the substrate comprises tissue.

15. The method of claim 13 wherein the attraction compound is associated with the substrate by chemical binding.

16. The method of claim 15 wherein the attraction compound is associated with the substrate by crosslinking.

17. The method of claim 15 wherein the attraction compound is associated with the substrate with specific binding interactions.

18. The method of claim 13 wherein the attraction compound is associated with the substrate by direct attachment.

19. The method of claim 13 wherein the attraction compound is associated with the substrate with an adhesive.

20. A prosthesis comprising a substrate with an associated attraction compound, the attraction compound binding viable endothelial cell precursor cells, wherein the attraction compound is not a growth factor.

21. The prosthesis of claim 20 wherein the attraction compounds are selected from the group consisting of antibodies, antibody fragments, humanized antibodies, ligands for CD 34 antigen, ligands for endoglin, ligands for $\epsilon$-selectin, and ligands for CD31.

22. The prosthesis of claim 20 wherein the attraction compound has an affinity constant less than about $10^{-10}$ moles/liter.

23. The prosthesis of claim 20 wherein the attraction compounds comprise a ligand for angioblast cell surface receptors.

24. The prosthesis of claim 20 wherein the prosthesis is a heart valve prosthesis.

25. The prosthesis of claim 20 wherein the substrate comprises uncrosslinked tissue.

26. The prosthesis of claim 20 wherein the substrate comprises crosslinked tissue.

27. The prosthesis of claim 20 wherein the substrate comprises a fabric.

28. The prosthesis of claim 20 wherein a growth factor, distinct from the attraction compound, is associated with the substrate.

29. A prosthesis comprising a substrate with an associated attraction compound and an associated response modifier distinct from the attraction compound, the attraction compound binding viable fibroblast precursor cells or viable endothelial precursor cells with the substrate.

30. The prosthesis of claim 29 wherein the attraction compound binds viable fibroblast precursor cells with the substrate.

31. The prosthesis of claim 29 wherein the attraction compound binds viable endothelial cells with the substrate.

32. The prosthesis of claim 29 wherein the response modifier comprises compounds that promote cell differentiation.

33. The prosthesis of claim 29 wherein the response modifier comprises compounds that inhibit an inflammatory response.

34. The prosthesis of claim 29 wherein the prosthesis is a heart valve prosthesis.

35. The prosthesis of claim 29 wherein the substrate comprises tissue.

36. The prosthesis of claim 29 wherein the substrate comprises synthetic polymers.

37. The prosthesis of claim 29 wherein the attraction compound comprises antibodies.

38. The prosthesis of claim 29 wherein the attraction compound comprises a ligand.

* * * * *